(12) United States Patent
Tanaka

(10) Patent No.: US 10,281,633 B2
(45) Date of Patent: May 7, 2019

(54) LIGHT SOURCE DEVICE AND LUMINAIRE

(71) Applicant: PANASONIC INTELLECTUAL PROPERTY MANAGEMENT CO., LTD., Osaka (JP)

(72) Inventor: Kenichiro Tanaka, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/977,366

(22) Filed: May 11, 2018

(65) Prior Publication Data

US 2018/0329130 A1 Nov. 15, 2018

(30) Foreign Application Priority Data

May 12, 2017 (JP) ................. 2017-096010

(51) Int. Cl.
| | |
|---|---|
| *F21V 8/00* | (2006.01) |
| *F21S 41/24* | (2018.01) |
| *F21S 41/16* | (2018.01) |
| *G02B 23/24* | (2006.01) |
| *F21S 41/176* | (2018.01) |
| *F21W 131/411* | (2006.01) |
| *F21W 131/105* | (2006.01) |
| *F21Y 115/30* | (2016.01) |

(52) U.S. Cl.
CPC ............ *G02B 6/0003* (2013.01); *F21S 41/16* (2018.01); *F21S 41/176* (2018.01); *F21S 41/24* (2018.01); *G02B 23/2469* (2013.01); *F21W 2131/105* (2013.01); *F21W 2131/411* (2013.01); *F21Y 2115/30* (2016.08)

(58) Field of Classification Search
CPC ... G02B 6/0003; G02B 23/2469; F21S 41/24; F21S 41/176; F21S 41/16
See application file for complete search history.

(56) References Cited

U.S. PATENT DOCUMENTS

| | | | |
|---|---|---|---|
| 6,636,686 B1 * | 10/2003 | Belfer .................. | G02B 6/0003 362/554 |
| 2018/0289940 A1 * | 10/2018 | Spotnitz .................... | A61L 2/10 |
| 2018/0317751 A1 * | 11/2018 | Kuboi ...................... | A61B 1/00 |

FOREIGN PATENT DOCUMENTS

JP 2015-228371 12/2015

* cited by examiner

*Primary Examiner* — Anne M Hines
(74) *Attorney, Agent, or Firm* — Greenblum & Bernstein, P.L.C.

(57) ABSTRACT

A light source device according to an embodiment includes a solid-state light source, and an optical transmission fiber. The optical transmission fiber includes a wavelength conversion core, a light guide core, and a clad, the wavelength conversion core absorbing excitation light to generate a population inversion state of electrons and including a wavelength conversion material emitting wavelength converted light in a visible light region, the light guide core covering a periphery of the wavelength conversion core and transmitting the wavelength converted light from a first end face side to a second end face side, and the clad covering a periphery of the light guide core. In the optical transmission fiber, the wavelength converted light propagating in the light guide core generates stimulated emission, and the excitation light and the wavelength converted light amplified by the stimulated emission are emitted from the second end face.

12 Claims, 2 Drawing Sheets

LIGHT SOURCE DEVICE AND LUMINAIRE

INCORPORATION BY REFERENCE

The entire disclosure of Japanese Patent Application No. 2017-096010 filed on May 12, 2017 including specification, claims, drawings and abstract is incorporated herein by reference in its entirety.

TECHNICAL FIELD

The present disclosure relates to a light source device, and a luminaire including the light source device.

BACKGROUND

Japanese Unexamined Patent Application Publication No. 2015-228371 discloses an illumination light source device that includes a light source unit including a primary light source that emits primary light, a plurality of light conversion units including light conversion elements that convert optical properties of the primary light to generate secondary light, and a connecting portion that detachably connects the light conversion unit in a light guide path. Japanese Unexamined Patent Application Publication No. 2015-228371 discloses that a semiconductor laser is used as the primary light source, and a fluorescent material is used as the light conversion unit.

SUMMARY

Since heat generation becomes larger in light conversion units having a fluorescent material when the light conversion units are arranged at front and rear of the light guide path, as in the light source device disclosed in Japanese Unexamined Patent Application Publication No. 2015-228371, a heat radiation measure is required. It is assumed that if the light conversion unit is arranged on an incident side of the light guide path, an incidence rate of the converted light incident into the light guide path will become lower, and the light source efficiency is decreased. On the other hand, since the converted light is emitted at random if the light conversion unit is arranged on an emission side of the light guide path, an issue arises that a luminaire requires a large-size lens.

A light source device according to one aspect of the present disclosure includes: a solid-state light source; and an optical transmission fiber into which excitation light emitted from the solid-state light source is introduced from a first end face, wherein the optical transmission fiber includes: a wavelength conversion core that includes a wavelength conversion material for absorbing the excitation light to generate a population inversion state of electrons and emitting wavelength converted light in a visible light region; a light guide core that covers a periphery of the wavelength conversion core and transmits the wavelength converted light from the first end face side to a second end face side; and a clad that covers a periphery of the light guide core, wherein the wavelength converted light propagating in the light guide core generates stimulated emission, and the excitation light and the wavelength converted light amplified by the stimulated emission are emitted from the second end face.

A luminaire according to one aspect of the present disclosure includes the above-described light source device.

Advantageous Effects of Invention

A light source device according to one aspect of the present disclosure may reduce the temperature increase in use, and is excellent in directivity. A luminaire including the light source device does not require a heat radiation structure, for example, thereby making it possible to reduce the size of the lens and substantially downsize the luminaire.

BRIEF DESCRIPTION OF DRAWINGS

The figures depict one or more implementations in accordance with the present teachings, by way of example only, not by way of limitations. In the figures, like reference numerals refer to the same or similar elements.

Embodiments of the present disclosure will be described based on the following figures, wherein.

DESCRIPTION OF EMBODIMENTS

Hereinafter, a light source device and a luminaire according to an embodiment of the present disclosure will be described in detail with reference to the drawings. Note that it is originally assumed that components in a plurality of embodiments described below may be selectively combined. Figures used for reference in the description of the embodiments are schematically illustrated, and dimension ratios of components drawn in the figures should be determined with reference to the following description.

Figure 1:
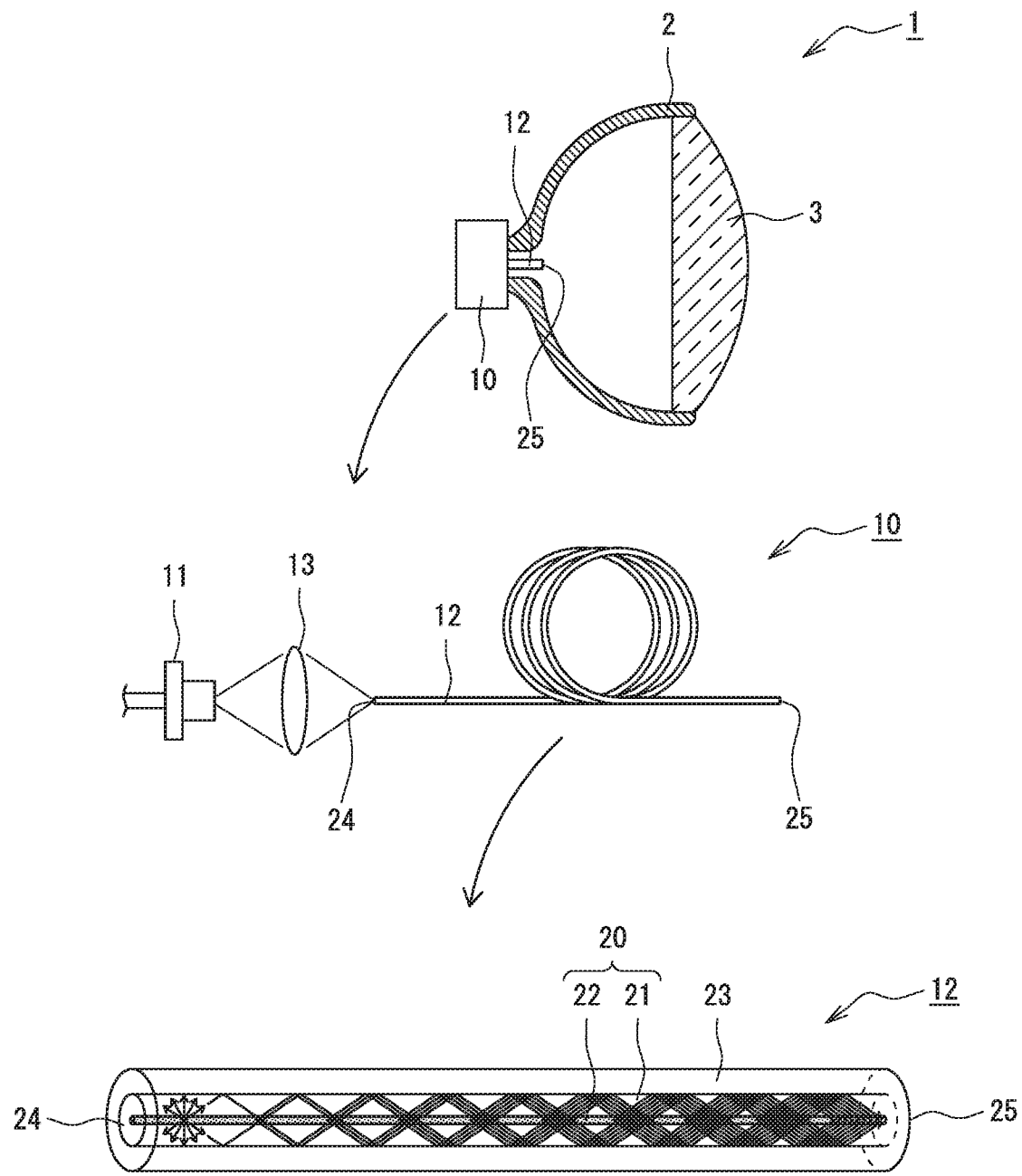
FIG. 1 is a view illustrating a light source device and a luminaire in an example of embodiments.

FIG. 1 is a view illustrating a light source device 10 and a luminaire 1 including the light source device 10 in an embodiment. The luminaire 1 exemplified in FIG. 1 includes a cylindrical case 2, a projection lens 3 that is attached to one axial end of the case 2, and the light source device 10 that is attached to the other axial end of the case 2. The case 2 has a shape with its diameter gradually increasing toward the projection lens 3 side, and has an inner surface functioning as a reflection surface for reflecting the light. The light source device 10 is arranged in a state where a second end face 25 of an optical transmission fiber 12 faces toward the projection lens 3 side. In the light source device 10, incoherent light is emitted from the second end face 25 of the optical transmission fiber 12.

The luminaire 1 that enables a heat radiation structure thereof to be simplified because of a small temperature increase of the light source device 10, and enables the projection lens 3 to be miniaturized because of excellent directivity of the light source device 10, is suitable for stadium illumination, a vehicular headlight, or the like. If the luminaire 1 is applied to stadium illumination, for example, the luminaire 1 that can remarkably reduce a wind receiving area (pressure receiving area) enables a support structure thereof to be simplified. Alternatively, the light source device 10 can be applied to an endoscope luminaire while making the best use of the advantage of small temperature increase of the light source device 10.

The light source device 10 includes a solid-state light source 11, and the optical transmission fiber 12 into which excitation light emitted from the solid-state light source 11 is introduced from a first end face 24. The optical transmission fiber 12 includes a core 20, and a clad 23 that covers a periphery of the core 20. The core 20 has a double core structure including a wavelength conversion core 21 and a light guide core 22, the wavelength conversion core 21 absorbing excitation light to generate a population inversion state of electrons and including a wavelength conversion material emitting wavelength converted light in a visible light region, and the light guide core 22 covering a periphery of the wavelength conversion core 21. The light guide core 22 transmits the wavelength converted light in the visible light region converted by the wavelength conversion material from the first end face 24 side to the second end face 25 side.

The light source device 10 is preferably provided with a lens 13 arranged between the solid-state light source 11 and the optical transmission fiber 12. The lens 13 is a condensing lens for efficiently introducing the light emitted from the solid-state light source 11 from the first end face 24 of the optical transmission fiber 12, for example. In the optical transmission fiber 12, the wavelength converted light propagating in the light guide core 22 generates stimulated emission, and the excitation light emitted from the solid-state light source 11 and the wavelength converted light amplified by the stimulated emission are emitted from the second end face 25.

The light source device 10 is different from a fiber laser in that reflection mirrors are not provided at both ends of the optical transmission fiber 12. Unlike the fiber laser, the light source device 10 does not emit light with a narrow spectrum width and having coherence, but emits white incoherent light. The light source device 10 has no wavelength conversion units including the wavelength conversion materials at both ends of the optical transmission fiber 12, but in the light source device 10, the wavelength conversion materials are dispersed in a lengthwise direction of the optical transmission fiber 12. This results in the light source device 10 having excellent heat radiation performance, thereby being unlikely to reach high temperature, even without the provision of a particular heat radiation structure. Note that the first end face 24 of the optical transmission fiber 12 may be provided with an optical filter that transmits the excitation light and reflects the wavelength converted light.

The solid-state light source 11 outputs the excitation light for exciting the wavelength conversion materials included in the wavelength conversion core 21 of the optical transmission fiber 12. Examples of the solid-state light source 11 include a light emitting diode (LED), an organic EL (OEL), and a semiconductor laser (LD). In the light source device 10, the semiconductor laser is preferably used for the solid-state light source 11 because the electrons in the wavelength conversion materials need to be brought into the population inversion state by introducing high-energy excitation light into the wavelength conversion core 21. A preferable example of the semiconductor laser is a semiconductor laser that outputs ultraviolet light, violet light or blue light having wavelengths of 250 nm to 480 nm.

A part of the excitation light emitted from the solid-state light source 11 is emitted from the second end face 25 through the optical transmission fiber 12. In the light source device 10, white light can be obtained by mixing the excitation light of the solid-state light source 11 and the wavelength converted light emitted from the wavelength conversion materials. The light emitted from the second end face 25 of the optical transmission fiber 12 is white incoherent light having broad spectral characteristics. On the other hand, the white light is amplified by the stimulated emission, and has excellent directivity.

The optical transmission fiber 12 has a structure in which the wavelength conversion core 21 having an approximately circular radial cross section at the center thereof, the tubular light guide core 22 arranged outward in the radial direction of the wavelength conversion core 21, and the clad 23, are arranged successively. The wavelength conversion core 21, and the light guide core 22, and the clad 23 are concentrically formed over the entire length of the optical transmission fiber 12. The optical transmission fiber 12 may have a protection film made of a resin that covers the periphery of the clad 23.

The optical transmission fiber 12 has a structure in which the core 20 is covered with the clad 23 having a refractive index lower than that of the core 20. The core 20 is composed of a quartz glass as a principle component, the quartz glass exhibiting small absorption losses of the excitation light introduced from the first end face 24 and the wavelength converted light generated from the excitation light absorbed by the wavelength conversion materials. The excitation light and the wavelength converted light propagate in the core 20 while being reflected at an interface between the core 20 and the clad 23. The clad 23 is also composed of a quartz glass as a principle component, similarly to the core 20. Note that the core 20 and the clad 23 may be made of a resin. For example, the core 20 may be made of an acrylic resin, and the clad 23 may be made of a fluorine resin.

The core 20 has a double core structure that includes the wavelength conversion core 21 including the wavelength conversion materials, and the light guide core 22 including no wavelength conversion material, as described above. Adopting such a double core structure enables the light guiding efficiency of the wavelength converted light to be improved. The stimulated emission is caused when the excitation light and the wavelength converted light propagating in the core 20 enter the wavelength conversion core 21, and the stimulated emission light is increased as it approaches the second end face 25 side of the optical transmission fiber 12. That is, the light emitted from the second end face 25 is amplified as the optical transmission fiber 12 becomes longer.

The length of the optical transmission fiber 12 is preferably 5 m or longer, and is more preferably 10 m or longer. The length and diameter of the optical transmission fiber 12 may be appropriately changed depending on the use of the luminaire 1 to which the light source device 10 is applied. If the luminaire 1 is used for stadium illumination, for example, the length of the optical transmission fiber 12 is preferably 10 m to 30 m, and the diameter of the optical transmission fiber 12 is preferably 1 mm to 3 mm.

The wavelength conversion materials are included over the entire length of the wavelength conversion core 21. The wavelength conversion core 21 has a structure in which the wavelength conversion materials are dispersed around a center shaft made of a quartz glass or an acrylic resin, for example. The concentration of the wavelength conversion materials is preferably approximately uniform over the entire length of the wavelength conversion core 21. In the light source device 10, the wavelength conversion materials generate heat in the process of absorbing the excitation light and emitting the wavelength converted light, but the wavelength conversion materials being heat generation sources are dispersed in the lengthwise direction of the optical transmission fiber 12, thereby suppressing the temperature increase of the light source device 10.

The wavelength conversion material is not limited to particular materials if the material absorbs the excitation light emitted from the solid-state light source 11 to generate the population inversion state of electrons and emits the wavelength converted light in the visible light region, and can be dispersed in the quartz glass or the resin of which the wavelength conversion core 21 is made. In other words, it is necessary to introduce the high-energy excitation light capable of generating the population inversion state of the wavelength conversion material into the wavelength conversion core 21. A conventionally well-known fluorescent material can be used for the wavelength conversion material.

The wavelength conversion material is preferably composed of a material having an excitation life (i.e., a time for which electrons stay at an excitation level) of 1 μs or longer as a principle component. In this case, the stimulated emission is easily caused, and the wavelength converted light is easily amplified. Plural types of fluorescent materials may be used as the wavelength conversion materials without causing problems in emitting light from the wavelength conversion materials, and fluorescent materials having an excitation life of 1 μs or longer and fluorescent materials having a short excitation life may be used in combination. In the wavelength conversion core 21, the fluorescent materials having the excitation life of 1 μs or longer may be included at 50 wt % to 100 wt % based on the total weight of the wavelength conversion materials.

A preferable example of the wavelength conversion material includes the following fluorescent materials (luminous pigments).

YAG:$Ce^{3+}$, YAG:$Cr^{3+}$
$Lu_3Al_2Ga_3O_{12}$:$Ce^{3+}$, $Lu_3Al_2Ga_3O_{12}$:$Cr^{3+}$
$Y_3Al_2Ga_3O_{12}$:$Ce^{3+}$, $Y_3Al_2Ga_3O_{12}$:$Cr^{3+}$
$Ga_3Al_2Ga_3O_{12}$:$Ce^{3+}$, $Ga_3Al_2Ga_3O_{12}$:$Cr^{3+}$
$M_2LnX_2(AlO_4)_3$

Where:

M includes any of Ca, Fe, Mn, Zn, Cd, Co, and Cu;

Ln includes any of Tb, Sc, Y, La, Ce, Pr, Nd, Sm, Eu, Gd, Dy, Ho, Er, Yb, Lu, In, and Sb; and X includes at least one of Zr and Hf, or at least one of Zr and Hf and at least one type selected from Si, Ge, Sn and Pb.

The fluorescent material includes Pr and at least one type selected from La, Eu, Dy, and Sm based on oxide represented by $A_aB_bO_c$.

Where:

A is at least one type selected from Ca, Sr, Ba, and Mg;

B is at least one type selected from Ti, Zr, Sn, Mn, Mo, and Ru; and $0.8 \leq a \leq 5$, $1.0 \geq b \geq 4$, $2.5 \geq c \geq (a+2b)$.

The light guide core 22 is a tube made of a quartz glass or an acrylic resin, for example, and is made of the same material as the wavelength conversion core 21. However, the wavelength conversion materials are not included in the light guide core 22. The wavelength converted light emitted from the wavelength conversion materials of the wavelength conversion core 21 propagates in the light guide core 22 from the first end face 24 side to the second end face 25 side, and sometimes enters the wavelength conversion core 21 and causes the stimulated emission.

The clad 23 is a tube made of a quartz glass or a resin having a refractive index lower than that of the core 20, for example. The clad 23 may have a photonic crystal structure. The photonic crystal structure is formed by including a plurality of pores periodically arranged in the fiber made of the quartz glass, for example. The plurality of pores are formed over the entire length of the optical transmission fiber 12. In this case, a part in which the plurality of pores are formed is the clad 23, and a part surrounded by the plurality of pores is the core 20. Note that the photonic crystal structure may be formed by periodically arranged a plurality of cylinders made of a material having a refractive index different from that of the core 20, instead of the pores.

In the light source device 10 configured as described above, the wavelength converted light is amplified in the process of propagating in the core 20 so that white incoherent light having high directivity in which the excitation light and the wavelength converted light are mixed is emitted from the second end face 25 of the optical transmission fiber 12. In the light source device 10, the wavelength conversion materials being heat generation sources are dispersed in the lengthwise direction of the optical transmission fiber 12, thereby reducing the temperature increase in use. The luminaire 1 including the light source device 10 does not require the heat radiation structure, for example, thereby making it possible to reduce the size of the lens and substantially downsize the luminaire 1.

Figure 2:
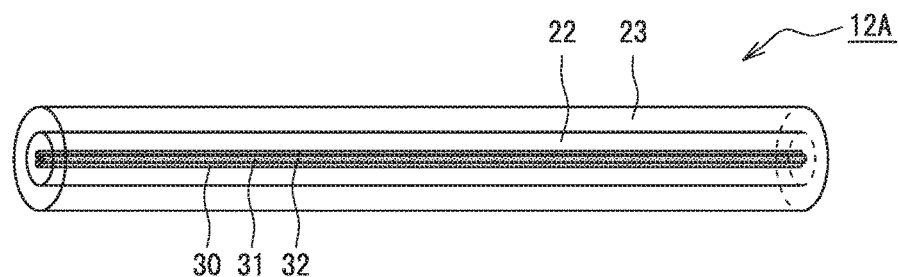
FIG. 2 is a view illustrating an optical transmission fiber of a light source device in another example of embodiments.
Figure 3:
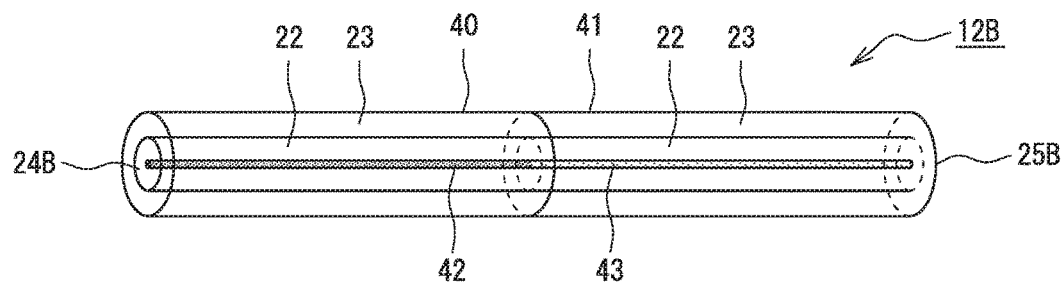
FIG. 3 is a view illustrating an optical transmission fiber of a light source device in another example of embodiments.
Figure 4:
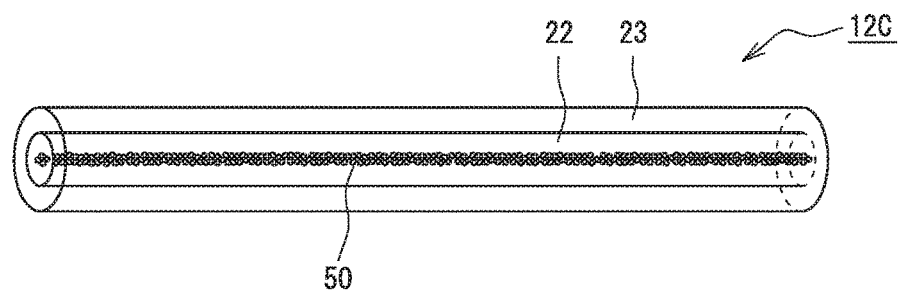
FIG. 4 is a view illustrating an optical transmission fiber of a light source device in another example of embodiments.

Hereinafter, a light source device according to another example of embodiments will be described with reference to FIG. 2 to FIG. 4. Hereinafter, differences from the above-described embodiment will be mainly described. FIG. 2 to FIG. 4 are views each illustrating an optical transmission fiber included in the light source device.

An optical transmission fiber 12A exemplified in FIG. 2 is different from the optical transmission fiber 12 having one wavelength conversion core 21 in that a plurality of wavelength conversion cores 30, 31, 32 are provided along the lengthwise direction. The wavelength conversion cores 30, 31, 32 are formed over the entire length of the optical transmission fiber 12A at the radially central part of the fiber 12A, and the periphery of each wavelength conversion core 30, 31, 32 is covered with the light guide core 22. The number of wavelength conversion cores is not limited to a particular number, and may be four or more, or two.

The wavelength conversion cores 30, 31, 32 preferably have wavelength conversion materials that are different from each other. This enables efficient multiple color conversion. The wavelength conversion materials, included in the respective wavelength conversion cores, each absorb excitation light emitted from the solid-state light source 11, and emit visible light having different wavelengths.

An optical transmission fiber 12B exemplified in FIG. 3 includes wavelength conversion materials having different excitation lives between the first end face 24B side and the second end face 25B side. In the example shown in FIG. 3, the optical transmission fiber 12B includes a first optical transmission fiber 40 having a first wavelength conversion core 42 and a second optical transmission fiber 41 having a second wavelength conversion core 43. The optical transmission fiber 12B is formed by joining the first optical transmission fiber 40 and the second optical transmission fiber 41 that have substantially same length and substantially same diameter, for example. In the optical transmission fiber 12B, the wavelength conversion materials are different from each other with a lengthwise direction center as a boundary, but the optical transmission fiber may include three or more types of wavelength conversion materials so as to be divided in the lengthwise direction of the optical transmission fiber.

The wavelength conversion material included in the second wavelength conversion core 43 preferably has an excitation life longer than that of the wavelength conversion material included in the first wavelength conversion core 42. That is, the wavelength conversion material included in the second end face side portion of the wavelength conversion core preferably has an excitation life longer than that of the wavelength conversion material included in the first end face side portion. In this case, the stimulated emission is easily caused, and the wavelength converted light is easily amplified. For example, a fluorescent material having an excitation life of 1 µs or longer may be added to the second wavelength conversion core 43, and a fluorescent material having an excitation life of less than 1 µs may be added to the first wavelength conversion core 42.

An optical transmission fiber 12C exemplified in FIG. 4 has a wavelength conversion core 50 formed of a plurality of particles each including wavelength conversion materials. The shape of the particles is not limited to particular shapes, and may be a spherical shape, or a rod-like shape. The wavelength conversion core 50 is formed of plural types of particles which absorb the excitation light emitted from the solid-state light source 11 and include the wavelength conversion materials emitting the visible light having different wavelengths, for example. This enables efficient multiple color conversion similarly to the optical transmission fiber 12A.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

The invention claimed is:

1. A light source device, comprising:
a solid-state light source; and
an optical transmission fiber into which excitation light emitted from the solid-state light source is introduced from a first end face,
wherein the optical transmission fiber includes:
a wavelength conversion core that includes a wavelength conversion material for absorbing the excitation light to generate a population inversion state of electrons and emitting wavelength converted light in a visible light region;
a light guide core that covers a periphery of the wavelength conversion core and transmits the wavelength converted light from the first end face side to a second end face side; and
a clad that covers a periphery of the light guide core,
wherein the wavelength converted light propagating in the light guide core generates stimulated emission, and the wavelength converted light amplified by the stimulated emission and the excitation light are emitted from the second end face.

2. The light source device according to claim 1, wherein the wavelength conversion core comprises a plurality of particles each including the wavelength conversion material.

3. The light source device according to claim 1, wherein the optical transmission fiber includes a plurality of the wavelength conversion cores provided along a lengthwise direction, and
the wavelength conversion cores include wavelength conversion materials that are different from each other.

4. The light source device according to claim 1, wherein the wavelength conversion material includes a material having an excitation life of 1 µs or longer as a principle component.

5. The light source device according to claim 1, wherein the wavelength conversion core includes wavelength conversion materials having different excitation lives between the first end face side and the second end face side of the optical transmission fiber, and
the wavelength conversion material included in the second end face side portion of the wavelength conversion core has an excitation life longer than that of the wavelength conversion material included in the first end face side portion.

6. The light source device according to claim 1, wherein the clad has a photonic crystal structure.

7. The light source device according to claim 1, wherein a length of the optical transmission fiber is 10 m or longer.

8. The light source device according to claim 1, wherein the solid-state light source is a semiconductor laser.

9. A luminaire, comprising the light source device according to claim 1.

10. The luminaire according to claim 9, wherein the luminaire is for stadium illumination.

11. The luminaire according to claim 9, wherein the luminaire is a vehicular headlight.

12. The luminaire according to claim 9, wherein the luminaire is an endoscope luminaire.

* * * * *